(12) United States Patent
Flyash et al.

(10) Patent No.: US 9,839,500 B2
(45) Date of Patent: Dec. 12, 2017

(54) APPARATUS FOR DENTAL TREATMENT

(71) Applicant: Colgate-Palmolive Company, New York, NY (US)

(72) Inventors: Lion Flyash, Nazareth Illit (IL); Kamal Khawaled, Shfaram (IL)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/172,983

(22) Filed: Feb. 5, 2014

(65) Prior Publication Data
US 2015/0044628 A1 Feb. 12, 2015

Related U.S. Application Data

(60) Provisional application No. 61/864,648, filed on Aug. 12, 2013.

(51) Int. Cl.
A61C 1/00 (2006.01)
A61C 17/16 (2006.01)
A61C 19/06 (2006.01)
A61C 17/20 (2006.01)
A61C 13/15 (2006.01)

(52) U.S. Cl.
CPC ............ A61C 17/16 (2013.01); A61C 17/20 (2013.01); A61C 19/066 (2013.01); A61C 19/003 (2013.01)

(58) Field of Classification Search
CPC ......... A61C 7/08; A61C 9/0006; A61C 19/06; A61C 19/063; A61C 19/066
USPC .......................... 433/6, 27, 80, 215–216, 229
See application file for complete search history.

(56) References Cited

U.S. PATENT DOCUMENTS

| 4,003,132 | A | * | 1/1977 | Beck | A61C 9/0006 433/214 |
| 4,237,574 | A | * | 12/1980 | Kelly | A46B 9/045 15/167.2 |
| 5,642,737 | A | * | 7/1997 | Parks | A61F 5/566 128/848 |
| 6,398,713 | B1 | * | 6/2002 | Ewing | A61N 2/008 600/9 |
| 6,893,259 | B1 | * | 5/2005 | Reizenson | A61C 17/0211 433/29 |
| 6,948,936 | B2 | * | 9/2005 | Miller | A61C 9/0006 433/214 |
| 7,775,795 | B2 | * | 8/2010 | Khawaled | A61C 19/066 433/214 |
| 7,810,503 | B2 | * | 10/2010 | Magnin | A61F 5/566 128/848 |
| 8,241,035 | B2 | * | 8/2012 | Jones | A61C 17/20 433/29 |

(Continued)

FOREIGN PATENT DOCUMENTS

JP 2012-110500 6/2012

Primary Examiner — Matthew Nelson

(57) ABSTRACT

An apparatus for treatment of teeth, including one or more dental treatment applicators having at least two walls and a floor, the walls and floor defining a well configured to accommodate at least one human dental arcade and an active agent, one or more energy-applying element located on at least one of the walls and wherein the improvement of the apparatus comprises paired dental treatment applicators configured to be applied to both upper and lower dental arcades concurrently and a number of dental treatment accelerating elements and fields.

18 Claims, 11 Drawing Sheets

(56) References Cited

U.S. PATENT DOCUMENTS

| | | | | |
|---|---|---|---|---|
| 2001/0012608 A1* | 8/2001 | Darnell | A61C 5/00 433/216 |
| 2005/0202363 A1* | 9/2005 | Osterwalder | A61C 9/0006 433/29 |
| 2006/0234189 A1* | 10/2006 | Duret | A61C 19/066 433/215 |
| 2007/0015112 A1* | 1/2007 | Hochman | A61B 8/546 433/215 |
| 2007/0276455 A1* | 11/2007 | Fiset | A61C 19/066 607/91 |
| 2008/0003540 A1* | 1/2008 | Khawaled | A61C 19/066 433/215 |
| 2008/0008978 A1* | 1/2008 | Conrad | A61C 19/06 433/32 |
| 2008/0199830 A1* | 8/2008 | Fontenot | A46B 5/0012 433/215 |
| 2008/0233541 A1* | 9/2008 | De Vreese | A61C 19/066 433/216 |
| 2009/0029311 A1* | 1/2009 | Chan | A61C 19/066 433/29 |
| 2009/0117513 A1* | 5/2009 | Nemeh | A61C 19/063 433/32 |
| 2009/0208543 A1* | 8/2009 | Nathoo | A61K 8/02 424/401 |
| 2010/0151407 A1* | 6/2010 | Rizoiu | A61C 17/20 433/29 |
| 2012/0244489 A1* | 9/2012 | Carnahan | A61B 8/0875 433/25 |
| 2012/0295218 A1* | 11/2012 | Moll | A61C 17/0211 433/32 |
| 2012/0322024 A1* | 12/2012 | De Vreese | A61K 8/362 433/29 |
| 2013/0004912 A1 | 1/2013 | Brown et al. | |
| 2013/0209964 A1* | 8/2013 | Nemeh | A61C 19/063 433/216 |
| 2014/0227657 A1* | 8/2014 | Sanders | A61C 19/066 433/32 |
| 2015/0037749 A1* | 2/2015 | Levine | A61C 19/063 433/27 |

\* cited by examiner

APPARATUS FOR DENTAL TREATMENT

TECHNICAL FIELD

The current method and apparatus relate to an apparatus for dental treatment and in particular to an apparatus for whitening teeth.

BACKGROUND

External appearance is important to practically every person. In recent years, methods and apparatuses have been developed for various dental treatments, namely fluorination of teeth as a preventative measure against tooth decay (e.g., tooth caries) and teeth whitening for aesthetic purposes.

'Whitening teeth' generally refers to application of any number of chemical and/or physical (mechanical) processes, procedures, or treatments, performed singly or in combination, which result in returning, and/or providing white color to teeth.

The chemical agents most commonly used for teeth whitening are oxidizing agents such as peroxides, some of which are activated when stimulated electrically, by heat and/or by light.

Application of chemical agents has been done in the past by using a "soaking" tray applied to a dental arcade for a given period of time wherein the teeth are brought into contact with the chemical agent. The treatment demanded much patience from the subject due to the length of time required for the chemical reaction to affect the teeth and moreover, in some cases—repeated treatments.

Attempts at changing the concentration of the chemical agent and/or the amount of time of exposure to the chemical agent, for whitening teeth, have been made. For example, some techniques (methods, devices) involve use of an electrical current to stimulate ion exchange, provide a thin conductive coating on the surface of the teeth, thereby enhancing the teeth conductivity. However, some of the existing techniques are typically based on using an electrical circuit which runs through a non-intra-oral cavity body part of an individual.

A typical chemical agent most commonly used for teeth whitening is hydrogen peroxide, although other relatively strong oxidizing agents, at appropriate concentrations and conditions of oral application are also commonly used for whitening teeth. Teeth are exposed to such strong oxidizing agents, whereby the oxidizing agents oxidize, and possibly also chemically degrade, substances which discolor teeth. However, applications of techniques for whitening teeth based on use of oxidizing agents, are typically accompanied by inadvertent or unpreventable, and undesirable, exposure of non-tooth intraoral cavity components, e.g., gum and tissue exterior surfaces, to the oxidizing agents. In some cases, applications of chemical or active agents is accompanied by application of a process or a material accelerating the bleaching or whitening action of the agent.

U.S. Pat. No. 6,340,301 discloses that the bleaching/whitening agents currently used in the art can be further activated by the constant application of heat to the bleaching/whitening agent, increasing the temperature of the bleaching/whitening agent above normal body temperature (98.6° F.) with a sub-sequential and consequential increase in the bleaching/whitening reaction, pursuant to the Q10 Rule, thereby activating and accelerating the bleaching/whitening process of stained or otherwise discolored teeth.

US Patent Application Publication No. 2003/0198605 discloses a method of whitening teeth employing a combination of an oxidizing composition and an accelerator that when exposed to a biologically safe and effective level of photoactinic light (e.g., UV light) the ability of the oxidizing compound in the whitening composition to effect rapid tooth whitening is enhanced.

U.S. Pat. No. 7,775,795 to Khawaled discloses an electrochemical method and a device for treating teeth. The method requires use of an activation solution such as a metal salt solution that is applied to teeth before the treatment to increase the tooth conductivity. Following the increase of the tooth conductivity an ionizable substance is applied to teeth. Electric current flows from a source of current to the teeth through a series of contacts applied directly to the teeth, so as to ionize the ionizable substance and reduce the tooth decay.

Techniques (methods, devices) currently employed could provide a uniform treatment throughout a dental arcade, but involve electric or mechanical contact with the treated teeth. Such contacts could result in certain uneasiness of the treated subject. Moreover, the techniques lack the ability to easy monitor treatment parameters, chemical quantities and rates of application applied to a dental arcade and a rapid response to gum irritation and subject discomfort should such occur.

SUMMARY

The present disclosure seeks to provide dental treatment applicators that can be fitted on either one of the upper and lower human dental arcades.

There are thus provided dental treatment applicators that include two parts—a portable unit and a dental treatment tray. The tray could be designed to be paired with a same or different dental treatment tray so that both dental treatment trays can be fitted at the same time (concurrently) onto their respective upper and lower dental arcades thereby treating both dental arcades concurrently and shortening treatment time.

The present disclosure also seeks to provide applicators for teeth whitening treatment that are operative to apply teeth whitening treatment.

There is thus provided a dental treatment applicator having one or more energy-applying elements that can be configured to accelerate the teeth whitening activity of teeth whitening agents applied to a portion of or the full dental arcade. Such energy-applying elements could apply an electric current to active or teeth whitening agent, emit in course of treatment light energy such as, for example, light emitting diodes (LED) and apply acoustic energy causing mechanical vibrations or magnetic fields.

In accordance with other examples, the energy-applying elements can be piezoelectric elements causing desired vibrations and/or a permanent or electromagnetic elements forming a magnetic field.

In accordance with one example, there is also provided a dental treatment applicator, and in particular a dental tray of the applicator, that can include electrodes configured to apply electric current to a whitening agent with a suitable electric conductivity. The whitening agent could be in a liquid or gel aggregate state. The electrodes could be immersed into a whitening or active agent with a suitable electric conductivity loaded into the tray. The electrodes could be adhered to walls of the tray by a suitable biocompatible adhesive or embedded inside the walls so as to have an exposed surface to create an electric current in the whitening or active agent with a suitable electric conductivity and wherein the exposed surface does not contact the teeth.

The DC-current flowing through the whitening agent, for example such a whitening gel or fluid with a suitable conductivity could also cause an oxidation reaction and a reduction reaction which is commonly referred to as a 'redox' reaction. The redox reaction involves an oxidizing agent suitable for use in teeth whitening procedure.

In accordance with another example the dental treatment tray of the dental treatment applicators can also include piezoelectric elements that could protrude from the dental treatment tray walls so that to come into contact with the gums when dental treatment applicator is applied to the dental arcade.

When activated, the piezoelectric elements can vibrate thus massaging the gums without the abrasive action commonly applied by apparatuses such as a tooth brush. The massaging effect can temporarily alleviate any discomfort or irritation brought about by the active agents, which could be in liquid or gel aggregate state, and/or oxidation process.

In accordance with another example, there is thus also provided a dental treatment applicator including a dental treatment tray with a well accommodating a dental arcade and active or whitening agent and piezoelectric elements that can be located so that not to come into contact with the gums when the dental treatment dental treatment applicator is applied to the dental arcade so that when activated, the piezoelectric elements can vibrate and assist in uniform distribution of the active agents throughout the well.

The present disclosure also seeks to provide dental treatment applicators that are operative to apply calculus removal treatment using, for example, piezoelectric elements.

In accordance with another example, there is thus also provided a dental treatment tray of a dental treatment applicator including piezoelectric elements that can effect acoustic-mechanical energy on calculus coating the teeth, generating cavitations in the fluid/liquid and causing the calculus to fracture, loosen and break away from the teeth enamel.

In accordance with another example, there is also provided a dental treatment tray of a dental treatment applicator that can also include permanent magnets adhered to walls of the applicator by a suitable biocompatible adhesive or embedded inside the walls so that to create a magnetic field inside the well defined by the walls of the tray and thus improve the teeth whitening process carried out by ions of the active or whitening agent.

In accordance with another example, there is also provided a method for teeth whitening treatment including applying to a dental arcade and active whitening agent, which could be in liquid or gel aggregate state, and activating the active agent by applying at least one form of energy selected from a group of forms of energy including light energy, electrical energy and acoustic-mechanical energy.

In accordance with another example, there is also provided applying a permanent magnetic field to the dental arcade while concurrently applying to the active agent electrical energy.

In accordance with another example the dental treatment applicators can also include a fluid conducting network configured for flushing and rinsing of the dental arcade being treated, removing fluid by suction or drying and soothing by blowing ambient air over the teeth and/or gums.

BRIEF DESCRIPTION OF THE DRAWINGS

The present method and apparatus will be understood and appreciated more fully from the following detailed description, taken in conjunction with the drawings in which.

DETAILED DESCRIPTION

In the current disclosure all dental treatment applicators described and illustrated as single dental arcade applicators can be fitted on either one of the upper and lower human dental arcades and the dental treatment trays can be designed to be paired with a same or different dental treatment tray so that both dental treatment trays can be fitted at the same time (concurrently) onto their respective upper and lower dental arcades thereby treating both dental arcades concurrently. Other features, as will be explained in greater detail below, include accelerating teeth whitening treatment using, for example, electric current, Light Emitting Diodes (LED), piezoelectric elements and/or a magnetic field and calculus removal employing primarily piezoelectric elements.

Figure 1A:
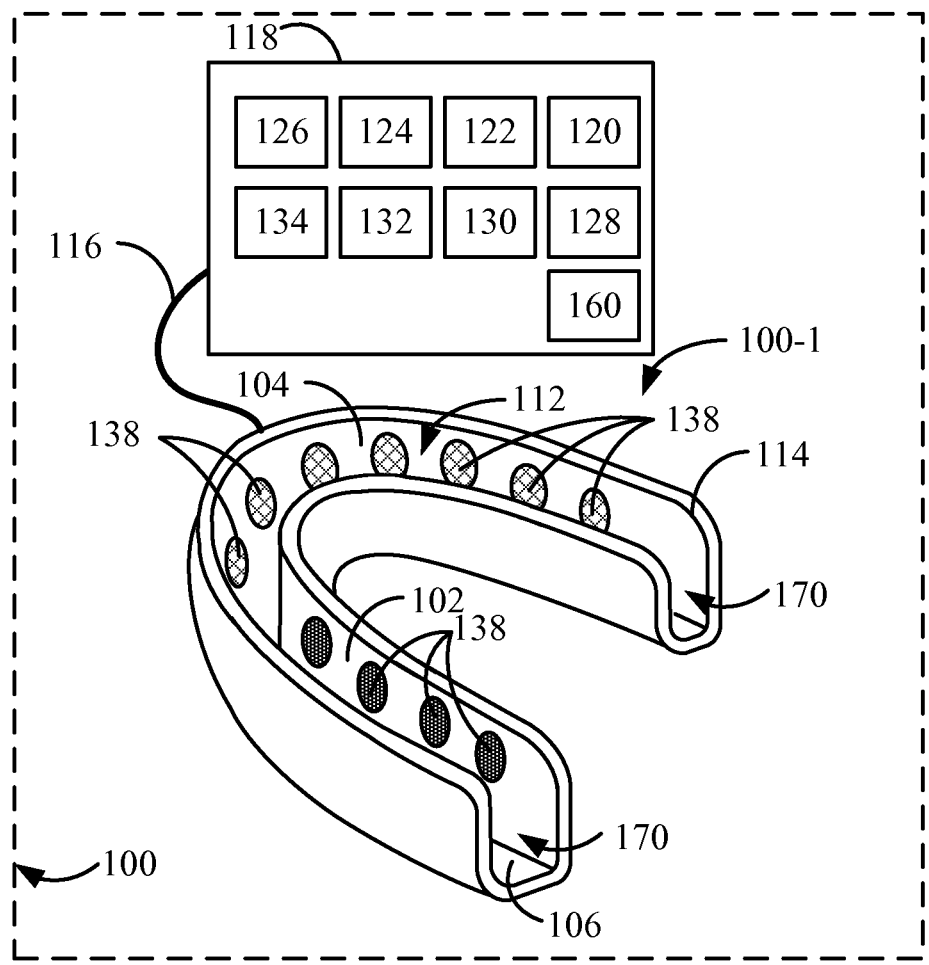
FIGS. 1A and 1B are perspective-view and block view simplified illustrations of an apparatus according to an example.
Figure 1B:
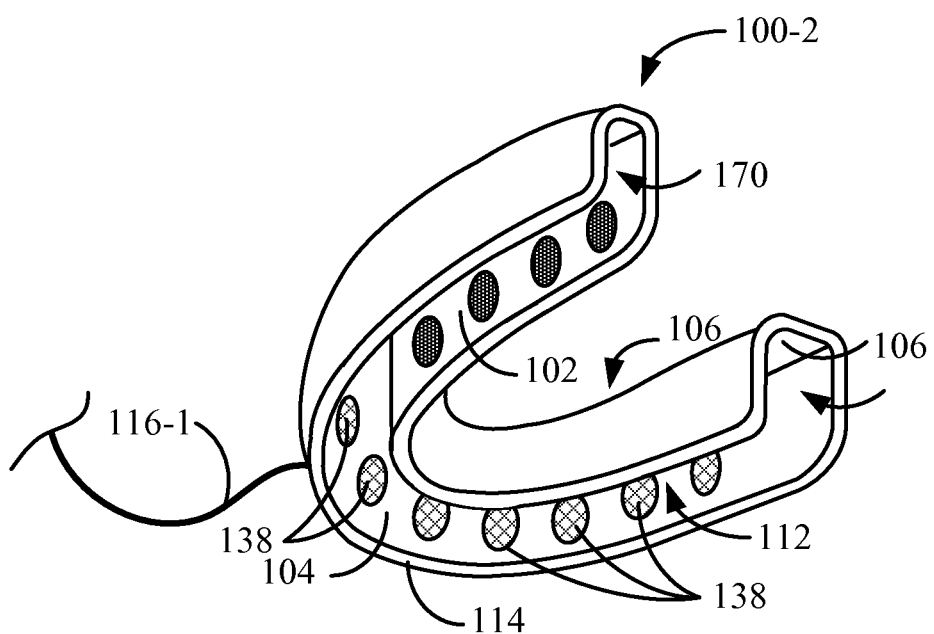

As shown in FIG. 1A dental treatment apparatus 100 could include a dental treatment applicator or tray 100-1 and a portable unit 118 that will be described in greater detail below. FIGS. 1A and 1B are perspective-view and block diagram simplified illustrations of an example, an upper dental arcade (FIG. 1A) and a lower dental arcade (FIG. 1B) dental treatment applicators or trays 100-1/100-2 can each be trough-shaped, curved in a form of a horseshoe so that to be configured to accommodate an upper or lower human dental arcade and an active agent. When paired, a pair of dental treatment applicators or trays 100-1/100-2 can be configured to accommodate both upper and lower dental arcades concurrently.

Dental treatment applicator or tray 100-1 (FIG. 1A) and 100-2 (FIG. 1B) could include a back curved wall 102 and a front curved wall 104 each integrally attached to opposite sides of floor 106 (FIG. 3) and together defining a well 112 configured to hold a substance such as, for example, an active or whitening agent (i.e., oxidizing chemical agent), which could be in liquid or gel aggregate state, with a suitable electric conductivity. Such as a suitable conductive active agent could be a teeth whitening liquid or gel with electric conductivity exceeding for example 200-400 microsiemens/cm. Use of such an active agent negates the need for an additional activating solution such as those used by the existing dental whitening devices. Walls 102/104 can also include energy-applying elements 138. Energy-applying elements 138 can be configured to emit in course of dental whitening treatment energy such as, for example, light energy from light emitting diodes (LED) 802 (FIGS. 8A and 8B) or electric energy such as, for example, applied by electric current electrodes 140/140-1 (FIGS. 6 and 7) as will be explained in greater detail below. Energy-applying elements 138 could be configured and commutated or controlled to address treatment of groups of teeth or individual teeth. The existing teeth bleaching or whitening devices provide a uniform treatment throughout a dental arcade and are not designed to provide varying degrees of treatment to individual teeth within a human dental arcade.

Since energy-applying elements 138 are employed to activate and/or accelerate the suitable conductive active or whitening agent, energy-applying elements 138 located on walls 102 and 104 do not have to come in contact with the teeth. In particular electric current flowing through the active agent from electrodes 140/140-1 could cause a redox reaction facilitating the teeth bleaching process.

A rim 114 can be optionally thickened and optionally covered with a resilient material so that when dental treatment applicator 100/100-1 is placed over and accommodates a dental arcade, rim 114 forms a seal with the gums and prevents leakage of the active agent and in particular of the active agent with suitable electric conductivity out of well 112. Optionally, rim 114 can be thickened and configured to extend beyond opening 140 up to a point of complete blockage, if desired, of opening 170. Dental treatment applicator 100/100-1 can be made of any biocompatible material, for example, such as clear plastic or silicone so that to facilitate view of the level of an active agent inside well 112.

Additionally and optionally, dental treatment applicators or trays 100-1/100-2 can also include a fluid conducting network similar to network 520 (FIG. 5) for flushing and rinsing the dental arcade being treated and others.

Dental treatment applicator or tray 100-1 could be connected via a harness 116 to a portable unit 118 that can include one or more of an alternating current (AC) or direct current (DC) power source 120, a DC-current generator 124. A computer or a processor 122, a suction/vacuum pump 126, a liquid reservoir 128, a gel reservoir 130, an ambient air fan 132 and a waste reservoir 134 could also be included in portable unit 118. Power source 120 could be, for example, a standard electrical AC grid outlet or a battery configured to supply energy-applying elements 138 and DC-current generator 124. DC-current generator 124 could be, for example, an alternating current (AC) rectifier or a battery. Some of the elements listed could be optional and not necessarily are included in each of the portable units 118. Active or whitening agent in liquid of gel aggregate state could be respectively stored and dispensed from liquid reservoir 128 or gel reservoir 130. Alternatively, the active agent could be manually filled in into well 112.

Portable unit 118 could also include one or more optional valves 160 configured to control flow of fluids such as the suitable active agents, water and ambient air through harness 116 conduits 150. Valves 160 can be in communication with and controlled by computer or processor 122.

Energy-applying elements 138 can be configured to communicate with one or more of computer 122, power source 120 and/or DC current generator 124.

Figure 1C:
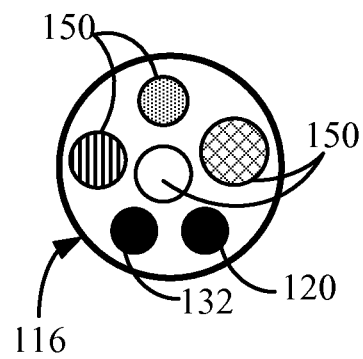
FIG. 1C is a cross-section view simplified illustration through a harness of FIGS. 1A and 1B.

As shown in FIG. 1C, which is a cross-section view simplified illustration through harness 116 of FIG. 1, harness 116 can also include one or more of electrical communication lines 120, data communication lines 132, conduits 150

Dental treatment applicator or tray 100-2 (FIG. 1B) could be paired (FIGS. 6 and 7) with dental treatment applicator 100-1 (FIG. 1A) and could be configured to connect directly to portable unit 118 via harness 116-1 or indirectly via dental treatment applicator or tray 100-1 as will be explained in greater detail below. Dental treatment applicator or tray 100-1 can be connected to harness 116 by one or more electrical and data communication connectors (not shown) such as, for example, a USB connector or any other suitable electrical and data communication connector known in the art and one or more fluid conduit connectors.

Figure 1D:
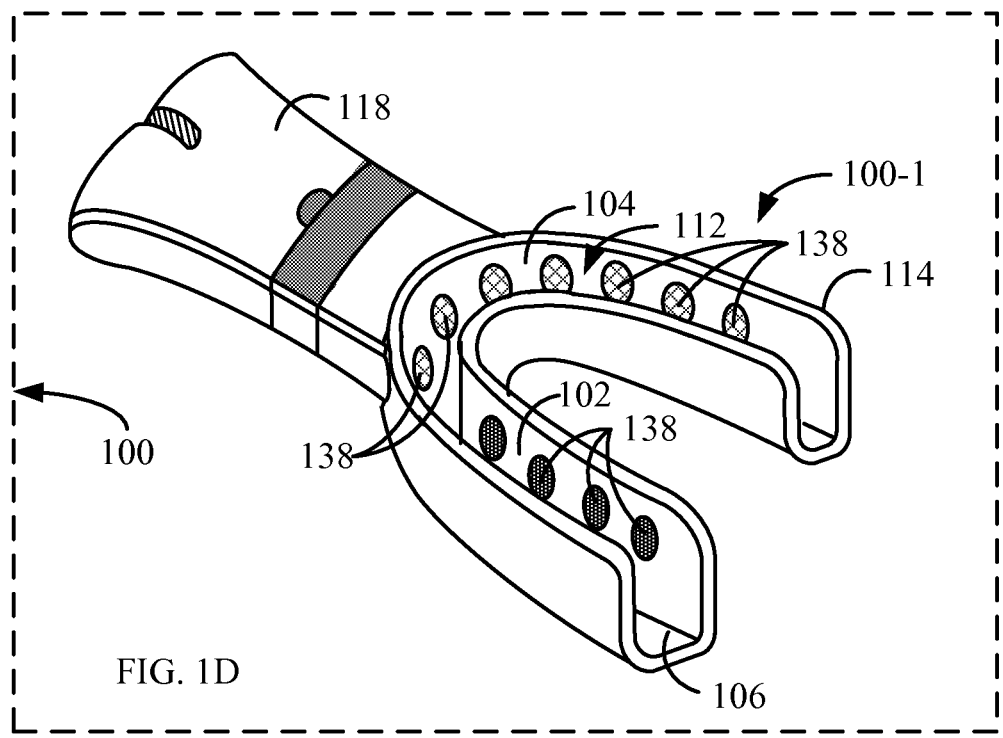
FIGS. 1D and 1E are perspective-view and exploded view simplified illustrations of another example.
Figure 1E:
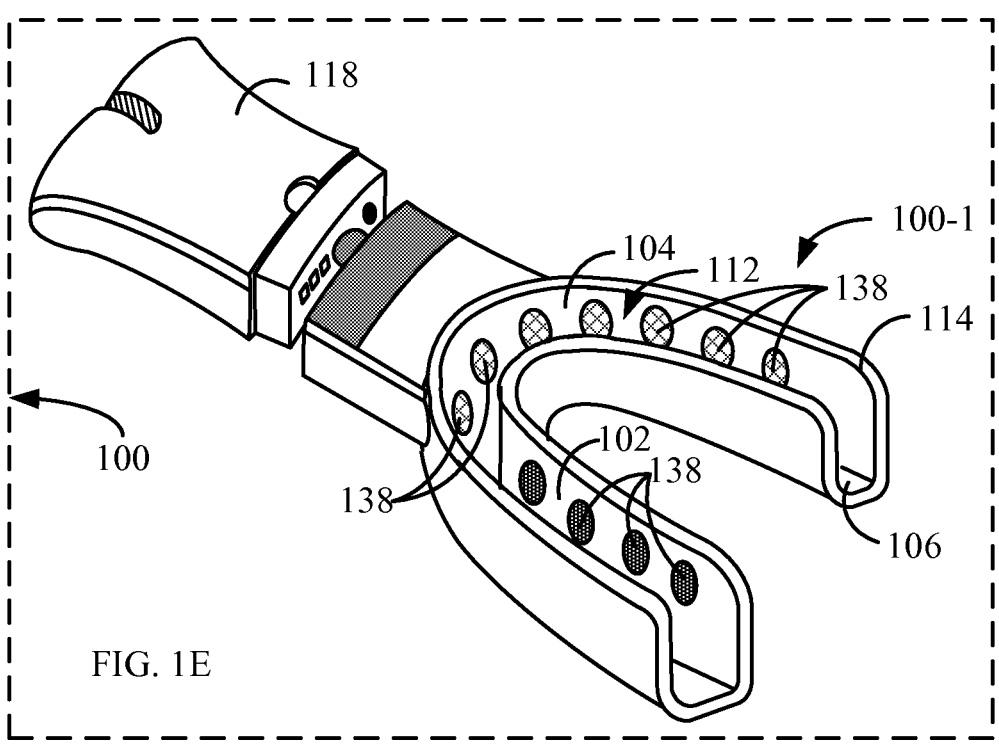

As illustrated in FIGS. 1D and 1E, which are perspective-view and exploded view simplified illustrations of another example of apparatus 100, where portable unit 118, is attached to dental treatment applicator or tray 100-1. In a basic implementation, portable unit 118 that could serve as a handle supporting a convenient handling of apparatus 100 and include one or more of alternating current (AC) or direct current (DC) power source 120. In some examples, portable unit 118 can be configured to implement a specific dental treatment protocol and could be replaced with another portable unit 118 when a different dental treatment protocol is desired.

Alternatively and optionally, portable unit 118 can include one or more disposable components such as liquid reservoir 128, gel reservoir 130 configured to supply the liquid or gel into well 112, waste reservoir 134 and power source 120 (FIG. 1A). As described above, portable unit 118 can serve as a handle and be attached to either one of dental treatment applicators or trays 100-1 and 100-2 or to both applicators 100-1 and 100-2. Portable unit 118 can be designed so that the user can close his or her lips comfortably around portable unit 118 during the treatment session.

Figure 2:
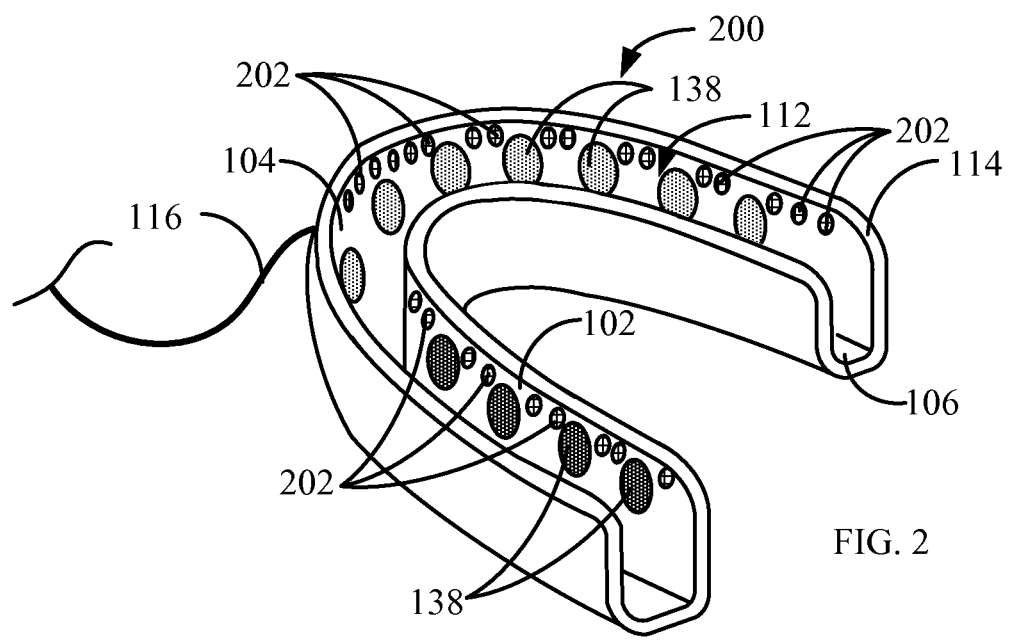
FIG. 2 is a perspective-view simplified illustration of still another example of a dental treatment dental treatment applicator.

In another example, illustrated in FIG. 2, which is a perspective-view simplified illustration of an example of a dental treatment applicator, dental treatment applicator or tray 200 can include piezoelectric elements 202 distributed along walls 102/104 at the level of the gums. Piezoelectric elements 202 can protrude from walls 102/104 so that to come into contact with the gums when dental treatment applicator 200 is applied to the dental arcade.

When activated, piezoelectric elements 202 can vibrate at a frequency of between 20 kHz and 36 kHz and in some examples between 20 kHz and 100 kHz and a power range between 0.02 to 2.0 watt per element, operative to apply a massaging effect to the gums without the abrasive action commonly applied by apparatuses such as a tooth brush. The massaging effect can temporarily alleviate any discomfort or irritation brought about by active agents and/or oxidation process inside well 112. Alternatively and optionally, piezoelectric elements 202 can be located along and protrude from walls 102/104 (e.g., at the level of the gums) so that not to come into contact with the gums when dental treatment applicator 200 is applied to the dental arcade (A layer of proper bio-compatible electrically insulating material could cover the piezo elements.). In this configuration, when activated, piezoelectric elements 202 can vibrate and assist in uniform distribution and mixing of the active agents throughout well 112 to accelerate their teeth whitening activity. The mixing activity of piezoelectric elements 202 can also replenish the active agents in areas where the active agent activity/concentration has been reduced by, for example, being diluted by saliva.

Additionally and optionally, piezoelectric elements 202 can vibrate at a frequency of between 20 kHz and 36 kHz and in some examples between 20 kHz and 100 kHz and a power range between 0.02 to 2.0 watt per element that can bring about superficial debridement of one or more gum cell layers thus stimulating inflamed gum tissue re-growth and healing.

Figure 3:
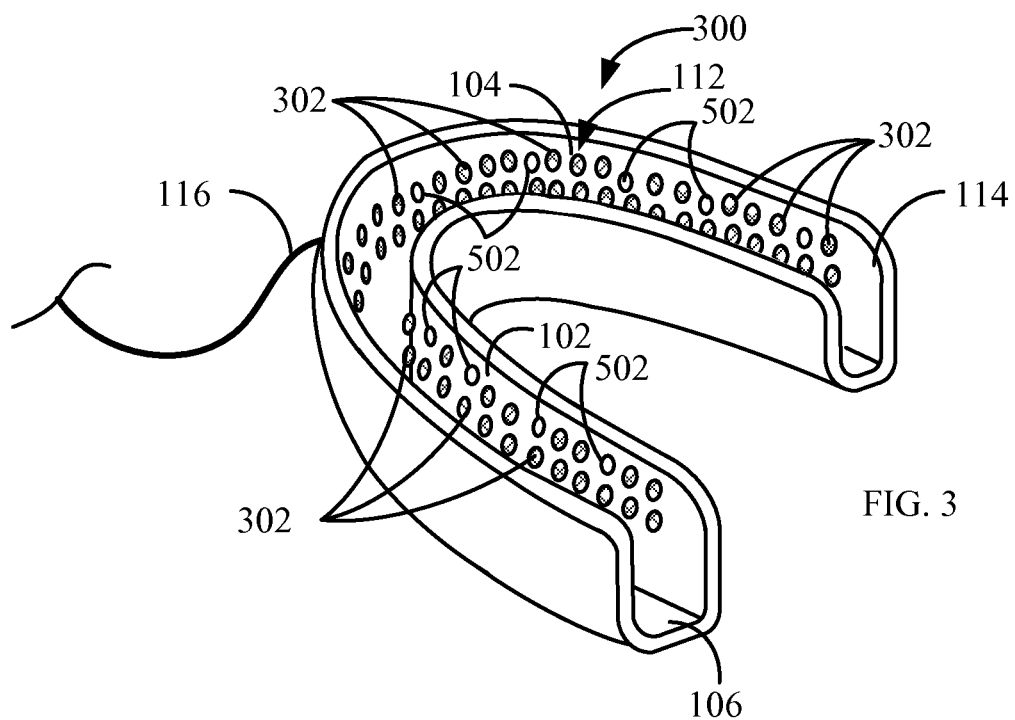
FIG. 3 is a perspective-view simplified illustration of another example of a dental treatment applicator.

FIG. 3, which is a perspective-view simplified illustration of yet another example of a dental treatment applicator. Applicator or tray 300 can be used as a dental scaler for calculus removal dental treatment. As illustrated in FIG. 3, piezoelectric elements 302 distributed along and protrude from walls 102/104 (e.g., at the level of the teeth) so that to come into contact with the teeth when dental treatment applicator or tray 300 is applied to the dental arcade.

When activated at a frequency of between 20 kHz and 36 kHz and in some examples between 20 kHz and 100 kHz and a power range between 0.02 to 2.0 watt per element, piezoelectric elements 302 can act as dental scalers by effecting acoustic-mechanical energy on calculus coating the teeth, generating cavitations in the surrounding fluid or liquid that in turn effect shock waves in the liquid causing the calculus to fracture, loosen and break away from the teeth enamel.

Cavitations induced by piezoelectric elements 302 can also enhance the effect of chemical reactions mainly because of the high energy created by the temperatures and pressure emitted by the large number of individual cavitation bubble implosions in the calculus and liquid.

In the presents of liquid, activation of piezoelectric elements 302 can generate vibrations inducing turbulent movement of the liquid that can help to remove the plaque from the tooth's surface and to flush out gum pockets. This activity can complement the cavitations-induced calculus removing activity. The turbulent movement of the liquid or gel could also be used to maintain a homogenous concentration of the active or whitening agent in well 112 and in some examples the piezoelectric elements 302 could be activated concurrently with the application of DC-current.

Dental treatment applicator 300 can also include multi-purpose apertures 502 (FIG. 5) that can be employed to flush well 112 with a liquid such as water stored in optional liquid reservoir 128 or gel reservoir 130 (FIG. 1A) during or after the calculus removal treatment. Flushing could also be employed to cool the teeth and gums from heat generated by piezoelectric elements 302. The flushing liquid can be removed by suction in the manner explained below.

Figure 4:
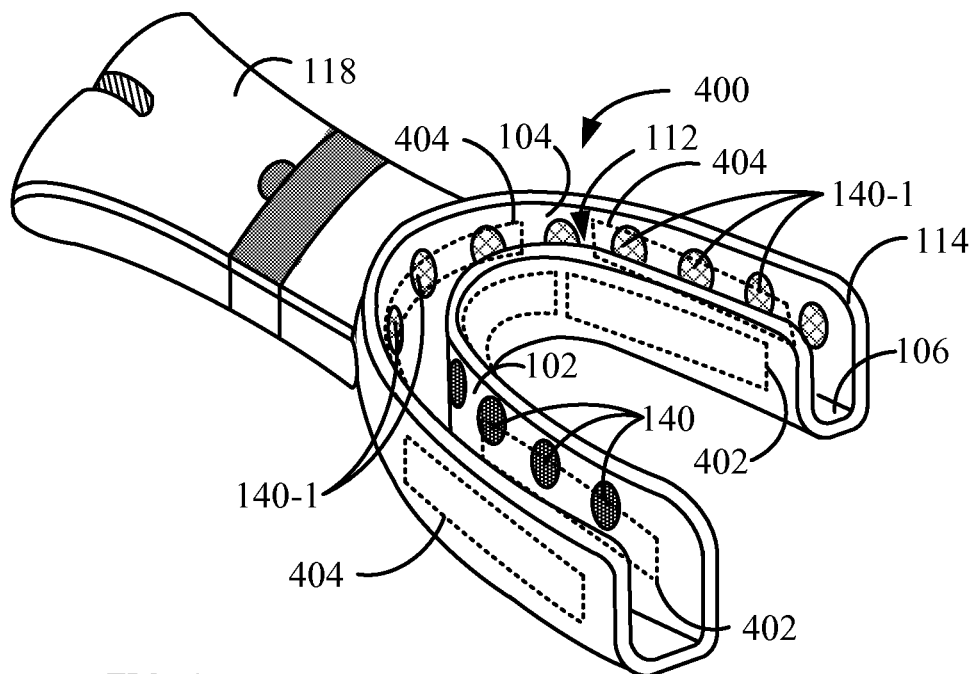
FIG. 4 is a perspective-view simplified illustration of yet another example of a dental treatment applicator.

Reference is now made to FIG. 4, which is a perspective view simplified illustration of another example of a dental treatment applicator. As described in *Water Electrolysis under a Magnetic Field* by T. Iida et al. (Journal of the Electrochemical Society 2007, vol. 154, no 8, [Note(s): E112-E115]), the energy efficiency of water electrolysis is considerably improved under a high magnetic field. Hence, application of electrolysis of the water based active or whitening agents (i.e., oxidizing chemical agents) under magnetic field conditions can intensify the process and speed it along, shortening the chair time of the subject being treated. As mentioned above, treating both dental arcades concurrently also contributes to shortening the chair time of the subject by at least halving the dental treatment time.

Dental treatment applicator 400 can also include permanent magnets 402/404 adhered to walls 102/104 by a suitable biocompatible adhesive or embedded inside walls 102/104 so that to create a magnetic field inside well 112 and thus improve the teeth whitening process carried out by, for example, by application of DC-current through electrodes 140/140-1.

Figure 6:
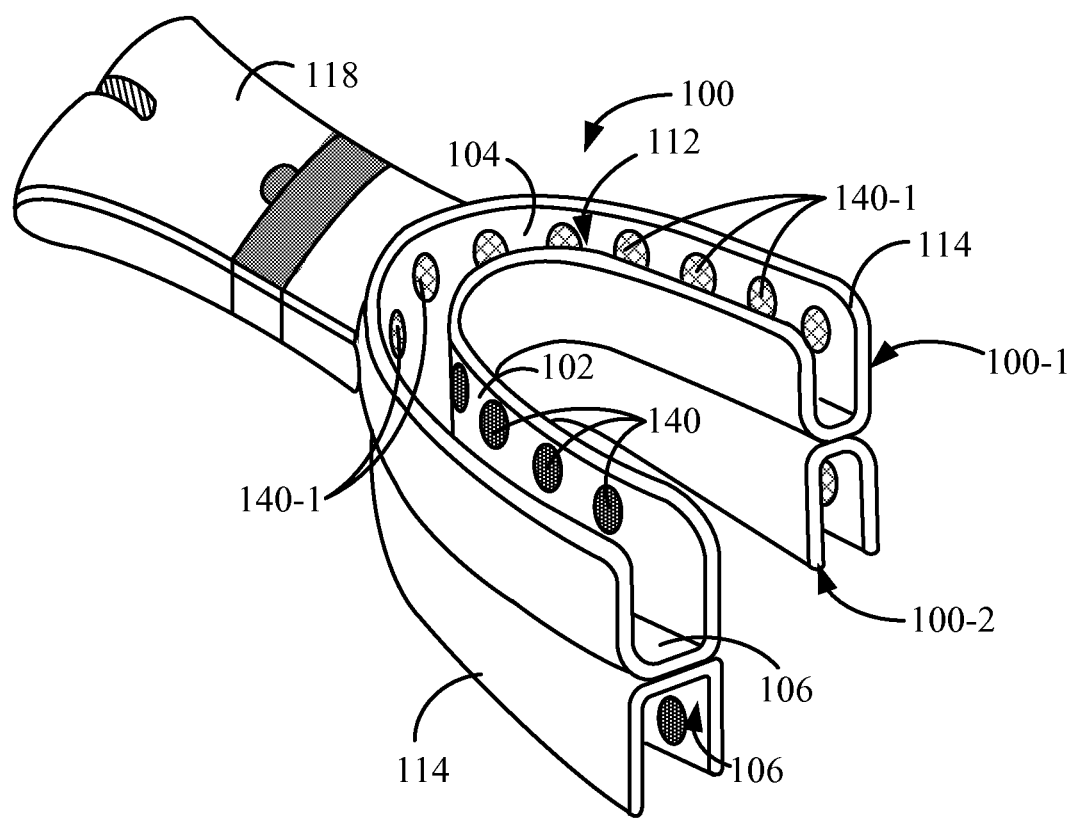
FIG. 6 is a perspective-view simplified illustration of yet another example of pairing of dental treatment applicators of FIGS. 1A and 1B.
Figure 7:
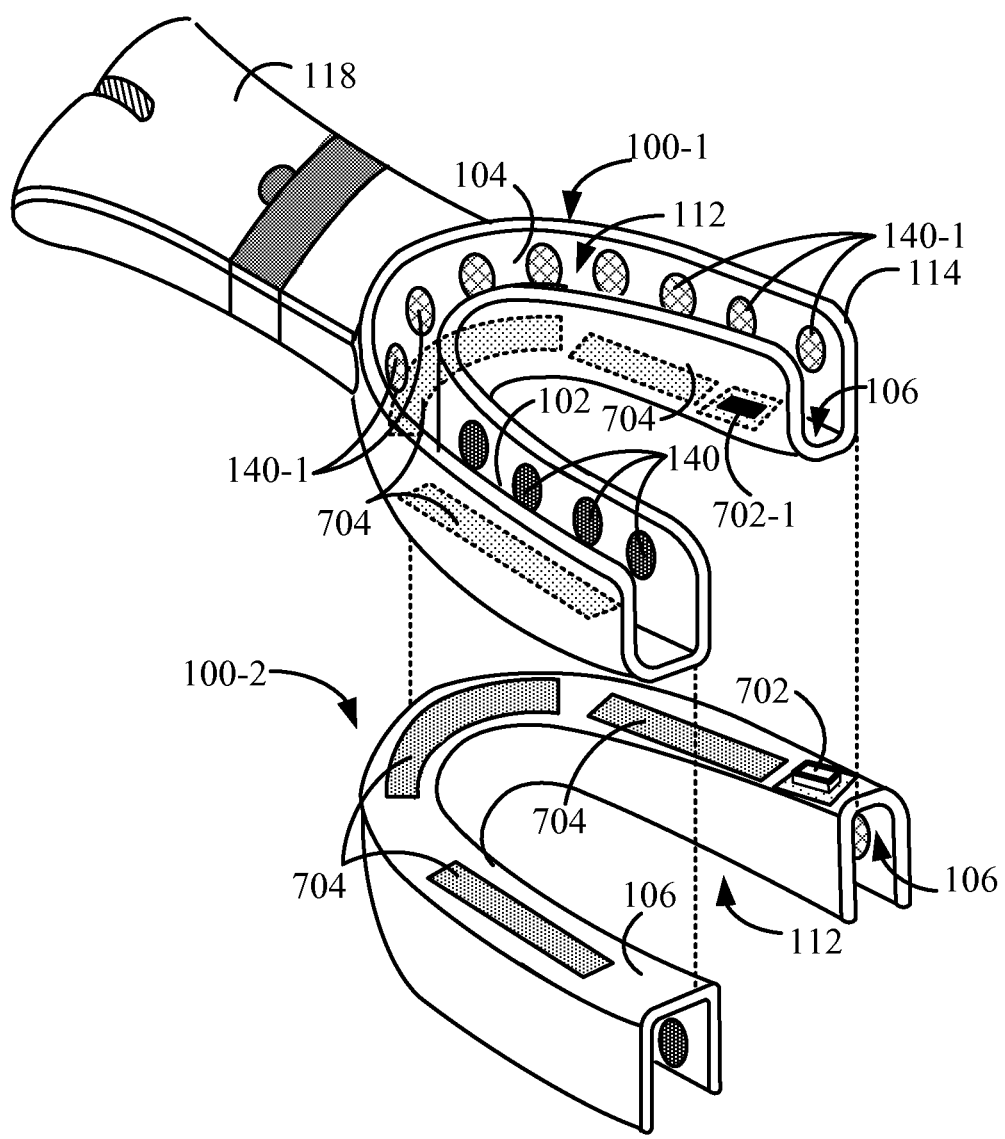
FIG. 7 is a perspective exploded-view simplified illustration of the example of FIG. 6.
Figure 8A:
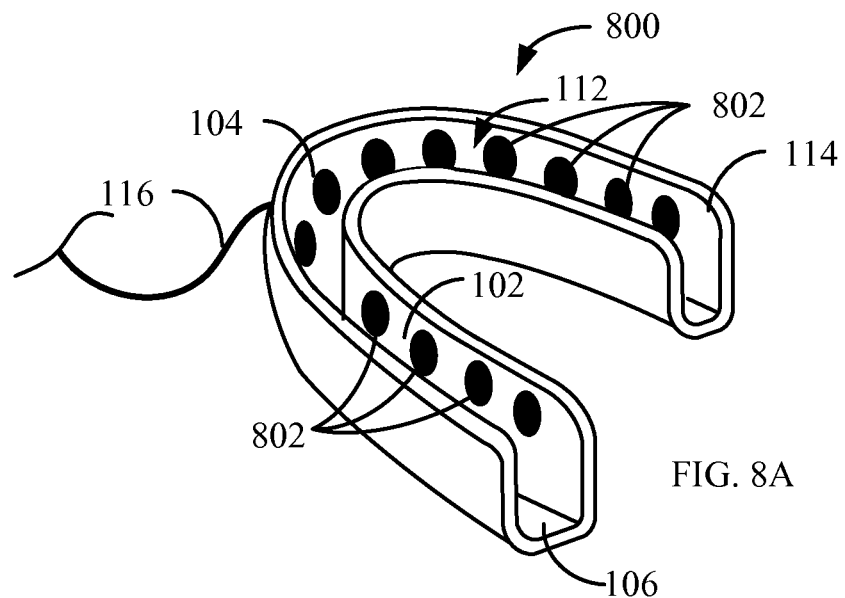
FIGS. 8A and 8B are perspective-view simplified illustration of still other examples of a dental treatment applicator.
Figure 8B:
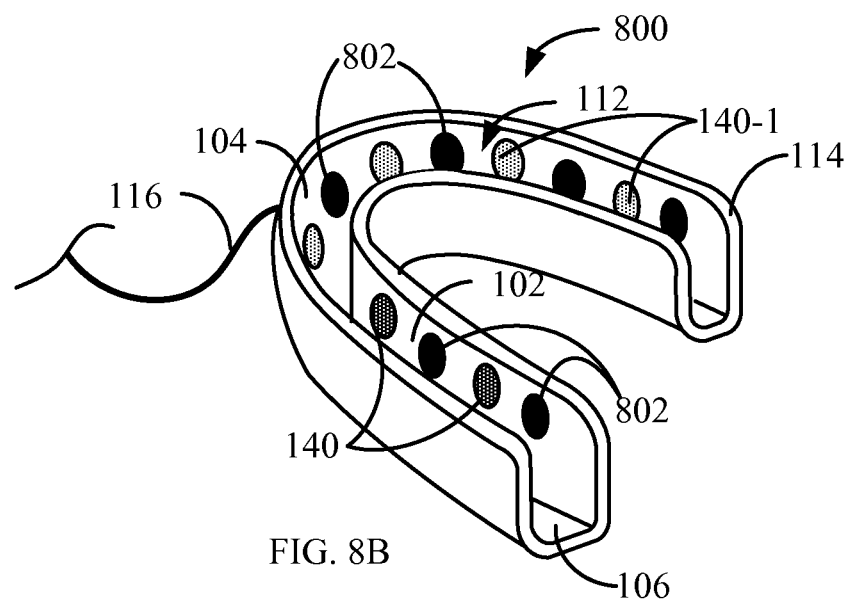

In some situations, employing permanent magnets in dental treatment applicator 400 can also simplify the treatment by effecting a magnetic field in well 112 directing the movement of free ions in liquid in well 112 thus negating the need for application of an electrical current to DC electrodes 140/140-1 (FIGS. 6, 7 and 8B).

Figure 5A:
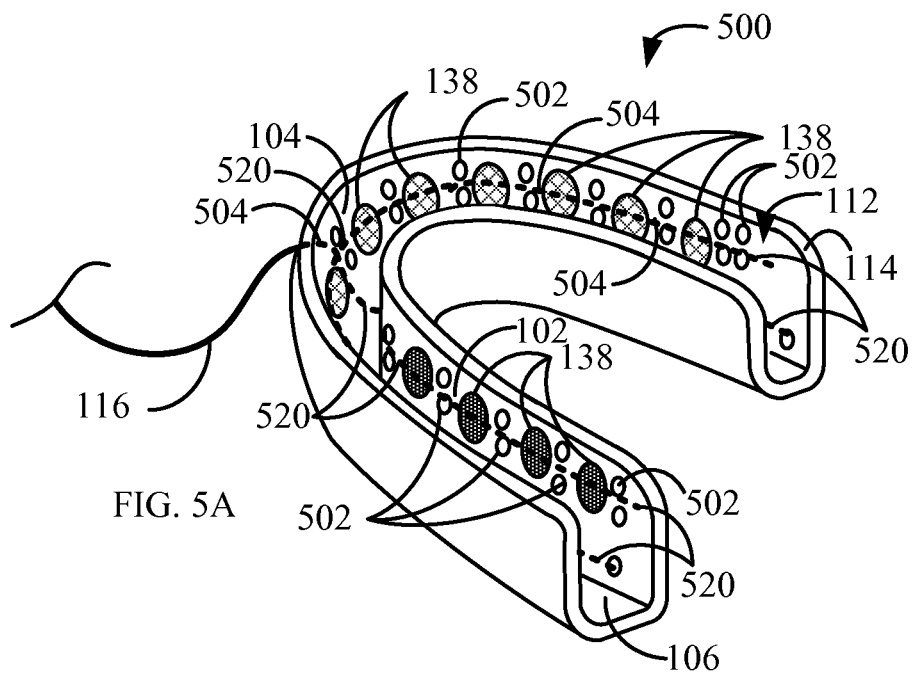
FIGS. 5A, 5B and 5C are perspective-view simplified illustrations of other examples of a dental treatment applicator.
Figure 5B:
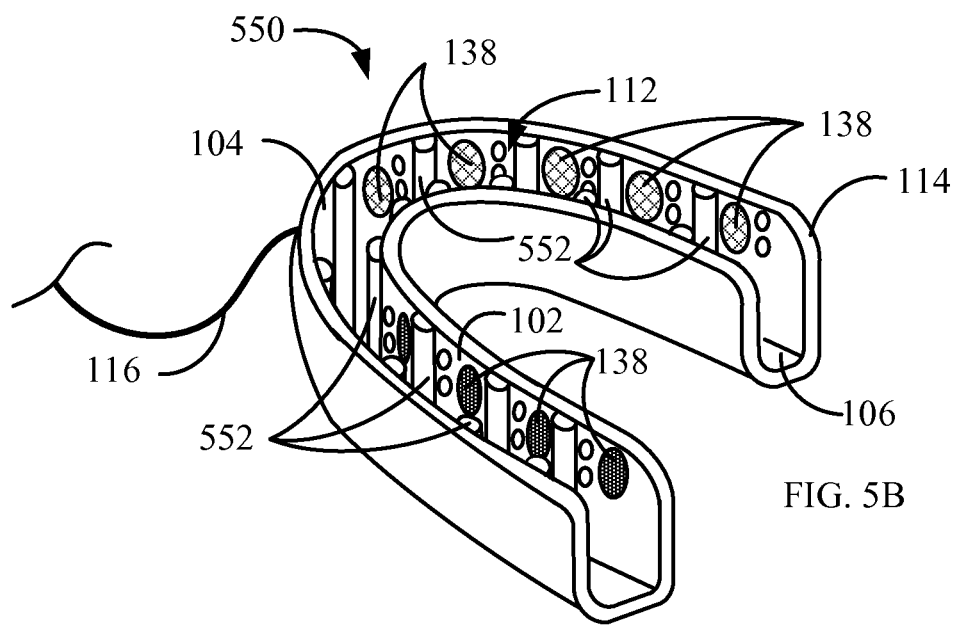
Figure 5C:
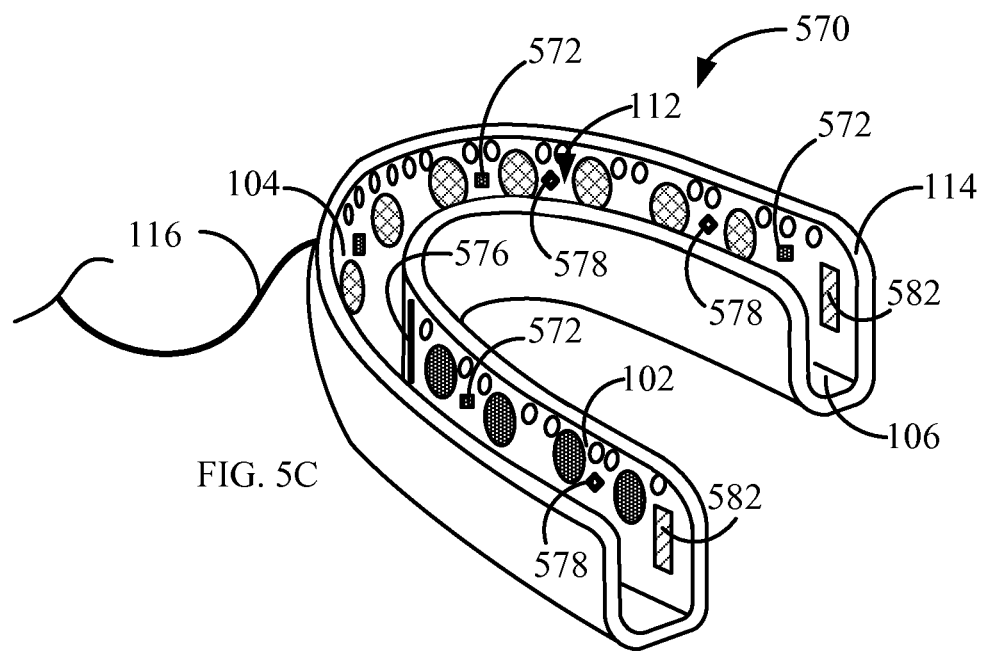

Reference is now made to FIGS. 5A, 5B and 5C, which are perspective-view simplified illustrations of still another example of a dental treatment applicator. As shown in FIG. 5A, dental treatment applicator or tray 500 can also include a fluid conducting network 520 configured, for example, for flushing and rinsing of the dental arcade being treated. The fluid conducting network 520 can include one or more multi-purpose apertures 502 in walls 102/104 that communicate with one or more common passages 504, depicted in FIG. 5A by phantom lines, inside and along walls 102/104 and floor 106 and communicate in turn with one or more liquid reservoir 128, gel reservoir 130 and waste reservoir 134 in portable unit 118 via dedicated conduits 150 (FIG. 1C) inside harness 116 or portable unit 118.

The fluid conducting network 520 and multi-purpose apertures 502 can act as nozzles to supply chemical oxidizing or active agents stored in liquid reservoir 128 or gel reservoir 130 (FIG. 1A), via one or more conduits 150 (FIG. 1C) in harness 116, through common passages 504 and into well 112. The amount of chemical oxidizing or fluorinating agents and rate of supply into well 112 can be controlled via one or more valves 160 (FIG. 1C) by computer or processor 122 (FIG. 1A) in accordance with a predetermined protocol.

Additionally or alternatively and optionally, the fluid conducting network 520 multi-purpose apertures 502 can act as intake ports, communicating with suction/vacuum pump 126 (FIG. 1A) via one or more conduits 150 (FIG. 1C) in harness 116 and common passages 504 to support rapid evacuation of well 112 from all liquid material into waste reservoir 134 (FIG. 1A). To avoid formation of vacuum in well 112, evacuation of liquid material could be immediately or concurrently followed by introduction of ambient air into well 112 by ambient air fan 132 (FIG. 1A) via one or more conduits 150 (FIG. 1C) in harness 116, common passages 504 and through multi-purpose apertures 502.

Additionally or alternatively and optionally, the multi-purpose apertures 502 of the fluid conducting network 520 could be employed to flush well 112 with a liquid such as water stored in liquid reservoir 128 or gel reservoir 130 (FIG. 1A), via one or more conduits 150 (FIG. 1C) in harness 116, through common passages 504 and into well 112. Flushing could also be employed to cool the teeth and gums from heat generated by energy-applying elements 138 when activating the active agents (i.e., oxidizing chemical agents) during treatment. The flushing liquid can be removed by suction in the manner explained above.

In another example depicted in FIG. 5B, dental treatment applicator 550 can also include two or more resilient partitions 552, positioned in pairs, distributed along walls 102/104 so that each partition on one of walls 102/104 is opposite its paired partition on the opposite wall 102/104 and normal to the plain of floor 106. Partitions 552 apportion walls 102/104 into segment pairs, each segment on one of walls 102/104 opposite its paired segment on the opposite wall 102/104. Each segment can include at least one DC current electrode and at least one multi-purpose aperture 502. The frequency of location of DC-electrodes and multi-purpose apertures could be configure to support treatment of each individual tooth. The electrodes are positioned so that not to contact adjacent teeth when the applicator is applied to the dental arcade.

In this example, computer or processor 122 (FIG. 1A) could be configured to control location and rate of suitable conductive active or whitening agents (e.g., oxidizing chemical agents with an electric conductivity higher than 200-400 microsiemens/cm) introduction and activation during treatment in accordance with a predetermined protocol preset by a user. Partitions 552 can be located in between two adjacent teeth such that each segment accommodates at least a single tooth, thus each tooth can be treated individually. In the case of teeth whitening for example, individual tooth treatment can compensate for uneven distribution of staining or discoloration of various teeth. Computer or processor 122 can be configured to control and adjust treatment of each individual tooth based on signals received from sensors in dental treatment applicator such as, for example, from an optic sensor 580 as will be explained further below.

The location of the fluid conducting network 520 multi-purpose apertures 502 along the height of walls 102/104 (i.e., the axis normal to plain of floor 106) can be determined and set for a specific treatment. As shown in FIG. 5C, multi-purpose apertures 502 can be distributed along the gum line only. This example can be employed, for example, for gum flushing and cooling purposes following a dental treatment session.

Dental treatment applicator 570, depicted in FIG. 5C can also include at least one sensor selected from a group of sensors including a temperature sensor 572, a liquid level gauge 576 such as, for example, a capacitance sensor, an oxygen sensor 578, an optic sensor 580 and a pH meter 582. The sensors can be configured to provide computer or processor 122 (FIG. 1A) with feedback including real-time treatment parameters regarding ongoing dental treatment. Computer or processor 122 could be configured to adjust treatment process based on treatment parameters received from sensors 572/576/578/580 and 582 by varying location and rate of active agents (e.g., oxidizing chemical agents) introduction and activation, stopping treatment altogether, evacuating well 112 from any material, flushing well 112 with flushing and/or cooling liquid or any other adjustment deemed necessary in accordance with the data received.

For example, optic sensor 580 can be a color verification sensor that can monitor changes in the color of a single tooth or multiple teeth and signal computer 122 (FIG. 1) when a desired level of whiteness has been achieved.

Alternatively or additionally and optionally when employing, for example, a dental treatment applicator such as that depicted in FIG. 5B, several optic sensors 580 can be configured to monitor color of individual teeth within a segment of a dental arcade or throughout a full dental arcade and provide computer 122 with information regarding the color of the individual teeth so that computer 122 can analyze color differences between various teeth based on signals received from optic sensor 580 and vary individual dental treatment accordingly.

Real-time treatment parameters can include one or more parameters selected from a group of parameters including temperature inside well 112, capacitance between the electrodes, impedance between the electrodes, level of activity (i.e., level of oxidation) of active agents, concentration of active agents inside well 112, color of teeth, level of liquid inside well 112 and others.

Reference is now made to FIGS. 6 and 7, which are perspective-view simplified illustrations of examples of pairing of dental treatment applicators or trays 100-1 and 100-2. As shown in FIG. 6, dental treatment applicators 100-1/100-2 can be paired and configured so that to comfortably accommodate both upper dental arcade and lower dental arcade concurrently thus at least halving the required dental treatment time (i.e., shortening dental treatment time by at least 50 percent).

Additionally and optionally, dental treatment applicators or trays 100-1/100-2 can each be operative to apply a different dental treatment to its corresponding dental arcade thus supporting application of different treatment protocols to different dental arcades concurrently negating the need for separate treatment times for each treatment protocol.

FIG. 7, which is an exploded perspective-view simplified illustration of paired dental treatment applicators or trays 100-1/100-2 of FIG. 2, depicts one or more electrical and data communication connectors 702/702-1 comprising male 702 and female 702-1 components, each located, for example but not necessarily, on floor 106 of each of the paired dental treatment applicators or trays 100-1/100-2. Electrical and data communication connector 702-1/702-2 facilitates electrical and data communication between dental treatment applicators 100-1/100-2 negating the need for dental treatment applicator 100-2 to connect directly to portable unit 118 and obviating harness 116-1 (FIG. 1).

Floors 106 of paired dental treatment applicators or trays 100-1/100-2 are configured to be removably attached to each other by attachments 704 facilitating easy attachment and detachment of dental treatment applicators 100-1/100-2 to and from one another. Attachments 704 can be, for example, strips of a mild adhesive allowing detachment of paired dental treatment applicators or trays 100-1/100-2 from one another by exertion of mild force or a fabric hook-and-loop fastener such as Velcro® (Velcro®, Amsterdam, The Netherlands). Alternatively and optionally, attachments 704 can be relatively weak magnets allowing detachment of dental treatment applicators 100-1/100-2 from each other by exertion of mild force. Attachments 704 are depicted on dental treatment tray 100-1 of FIG. 7 by phantom lines.

As known in the art, both fluorination and teeth whitening procedures benefit from ionization by electrolysis of fluorinating and oxidizing agents by running an electrical current therethrough. Additionally, agents such as peroxides undergo oxidation in the presence of moisture, proteinaceous material (oral tissues), light and/or heat. Hence, heat and light application to the active agents, which could be in liquid or gel aggregate state (i.e., oxidizing chemical agents) can activate the process, intensify it and speed it along, shortening the chair time of the subject being treated. As mentioned above, treating both dental arcades concurrently also contributes to shortening the chair time of the subject by at least halving the dental treatment time.

Reference is now made to FIG. 8A, which is a perspective-view simplified illustration of an example of a dental treatment applicator as depicted in FIG. 8A, dental treatment applicator or tray 800 energy-applying elements 138 of FIGS. 1A and 1B can be Light Emitting Diodes (LEDs) 802.

LEDs 802 can emit an effective level of actinic light (e.g., UV light) and activate active agents such as whitening compositions or fluorinating compositions introduced into well 112 to effect rapid tooth whitening or fluorine uptake by the teeth. Additionally, LEDs 802 also generate heat further intensifying the process, speeding it along and shortening the chair time of the subject being treated.

Referring back to FIGS. 4, 6, 7 and 8B, energy-applying elements 138 (FIGS. 1A and 1B) can be DC current electrodes 140/140-1 (FIGS. 4, 6, 7 and 8B) positioned on the inside surfaces of walls 102 and 104 and communicating with DC current generator 124 and computer 122 (FIG. 1A). The polarity of DC current electrodes 140 is opposite the polarity of electrodes 140-1, i.e., if DC current electrodes 140 have a negative polarity (cathode), electrodes 140-1 have a positive polarity (anode) and vice versa, maintaining a voltage therebetween and generating a current when an active agent with suitable electrical conductivity, for example, a teeth whitening gel or liquid, is placed in well 112, in contact with both electrodes 140 and 140-1.

When applying DC current energy to the dental arcade via DC current electrodes 140/140-1, in the presence of a suitable conductive whitening agent, fluid or gel, the current generated between the electrodes activates the oxidizing agent thus enhancing the agent's activity, accelerating the treatment. Additionally, DC current energy applied by DC current electrodes 140/140-1 generates heat within the active agent which could be a fluid or gel, further accelerating the treatment and shortening chair time of the subject being treated. Electrodes 140 and 140-1 are placed on walls 102 and 104 so that when treatment trays 100-1/100-2 are placed onto the respective dental arcades electrodes 140/140-1 contact only the fluid or gel with suitable electric conductivity and do not contact the teeth themselves. In such a configuration when using a suitable conductive gel that can be a gel having, for example, conductivity exceeding 200-400 microsiemens/cm, no additional activating agent or solution is required.

Alternatively and optionally and as depicted in FIG. 8B, dental treatment applicator 800 could include both DC current applying electrodes 140/140-1 and Light Emitting Diodes (LEDs) 802. LED's 802 can be activated to generate photoactinic light and generate heat to sensitize and begin activation of the whitening composition or fluorinating composition followed by electrodes 140/140-1 activation so that to bring about full activation of the active or whitening agent composition without further elevation of temperature of the active agent compositions and/or dental arcade (teeth and/or gums) and prevent discomfort to the subject being treated. In this configuration, LED's 802 and electrodes 140/140-1, controlled by computer or processor 122 that can address individually each tooth or segment of the dental arcade.

Figure 9A:
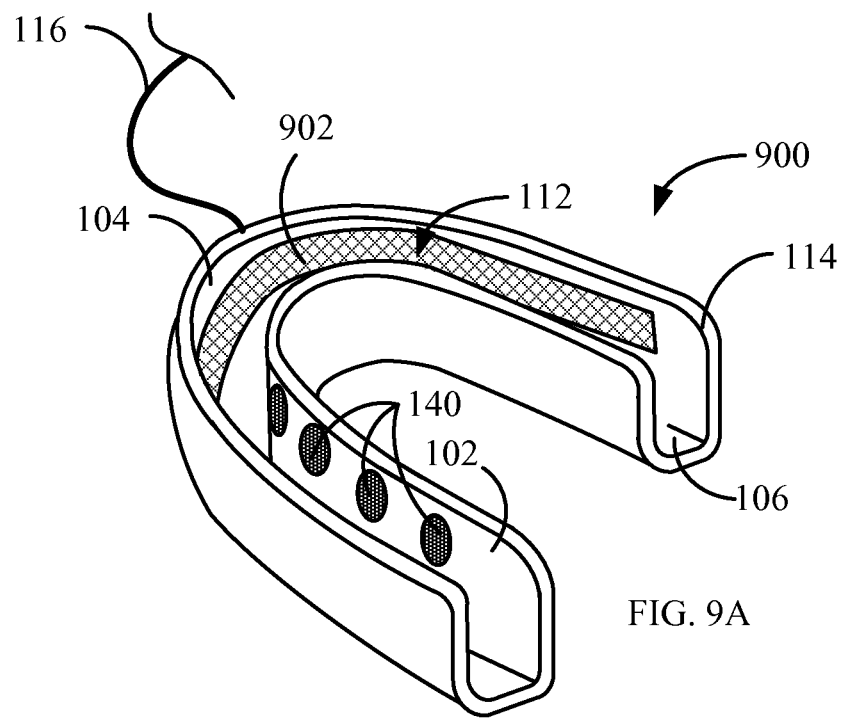
FIGS. 9A and 9B are perspective-view simplified illustrations of other examples of a dental treatment applicator.
Figure 9B:
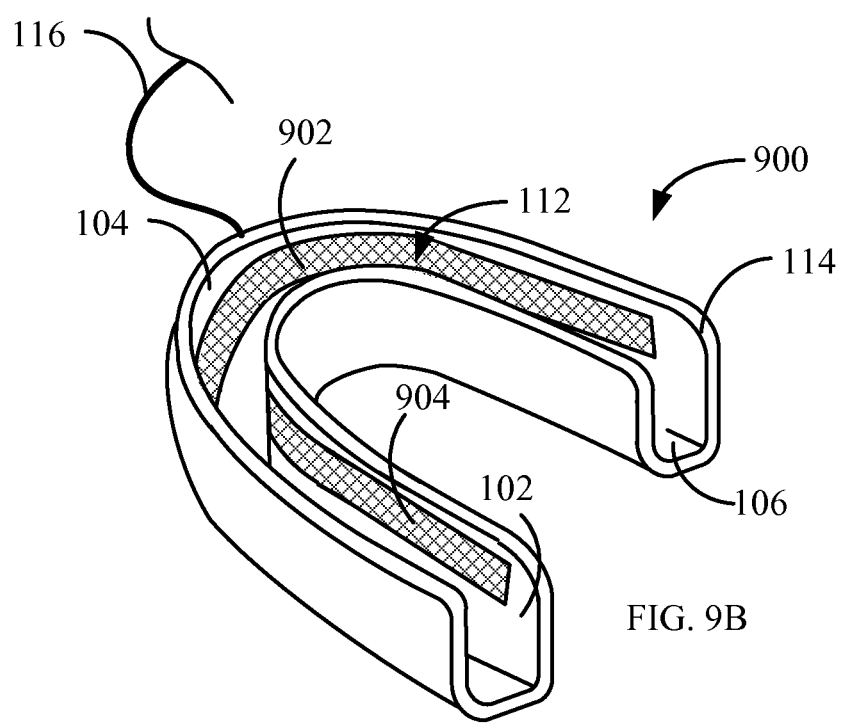

Alternatively and optionally, and as depicted in FIG. 9A, which is a perspective-view simplified illustration of another example of a dental treatment applicator, dental treatment applicator 800 one or more electrodes 902 can be in a form of an electrically conductive strip and placed along the curved surface of walls 102 and/or 104. In another configuration, shown in FIG. 9B, continuous electrodes in the form of electrically conductive strips 902/904 are placed on walls 104 and 102 respectively and in contact with only the fluid or gel with suitable electric conductivity and do not contact the teeth themselves. During treatment, electrodes 902/904 can be electrically connected to opposite electrical poles so to cause a redox reaction facilitating the teeth bleaching process.

Figure 10:
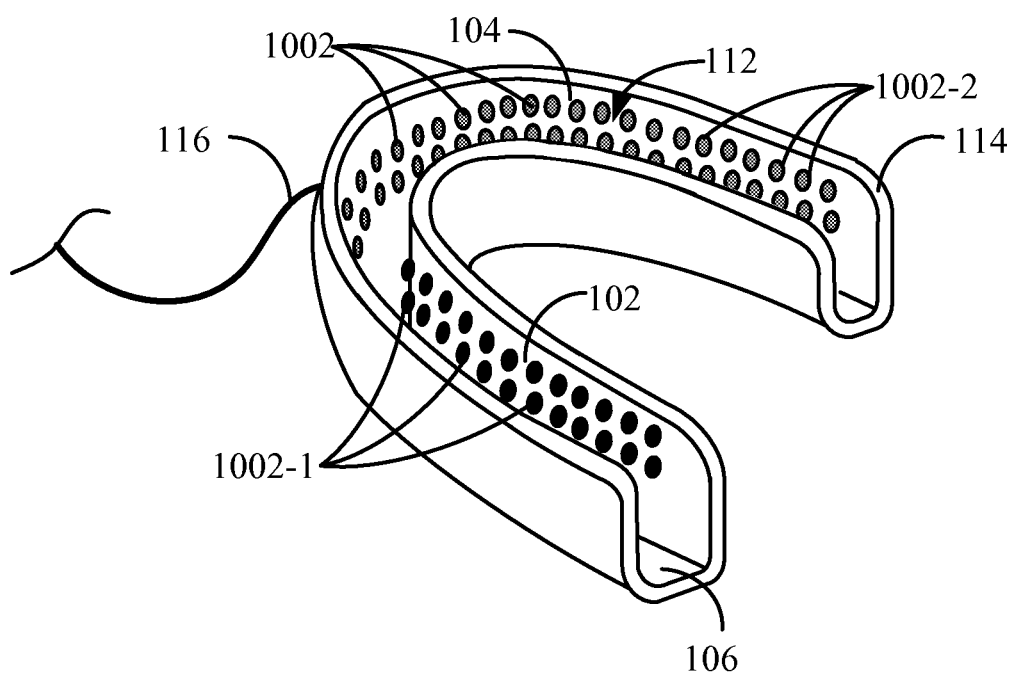
FIG. 10 is a perspective-view simplified illustration of still another example of a dental treatment applicator.

As shown in FIG. 10, which is a perspective-view simplified illustration of still another example of a dental treatment applicator energy-applying elements 138 of FIGS. 1A and 1B can be a plurality of DC current-applying elements 1002/1002-1.

The polarity of DC current-applying elements 1002 is opposite the polarity of DC current-applying elements 1002-1, i.e., if DC current-applying elements 1002 have a negative polarity (cathode), DC current-applying elements 1002-1 have a positive polarity (anode) and vice versa, maintaining a voltage therebetween and generating a current when an electrolytic chemical agent is placed in well 112, in contact with both DC current-applying elements 1002 and 1002-1.

Additionally and optionally, DC current-applying elements 1002-2/1002-1 can be individually supplied by DC current energy generator 124 and individually controlled by computer or processor 122 so that the DC current between pairs of DC current-applying elements 1002-2/1002-1 can vary at various locations along the dental arcade being treated by the activated whitening gel with suitable electric conductivity and apply treatment to one or more segments of the dental arcade or to individual teeth without being in contact with the teeth. For example, dental treatment can vary from treatment at discrete locations through regional activation (e.g., provide a gradient of level of activity along the dental arcade) to full dental arcade treatment of fluorination or whitening treatment to the teeth.

It will be appreciated by persons skilled in the art that the present method and apparatus are not limited to what has been particularly shown and described hereinabove. Rather, the scope of the method and apparatus includes both combinations and sub-combinations of various features described hereinabove as well as modifications and variations thereof which would occur to a person skilled in the art upon reading the foregoing description and which are not in the prior art.

What we claim is:

1. An apparatus for electro-chemical dental whitening, said apparatus comprising:
   a dental treatment tray configured to be applied to at least one of upper or lower dental arcades, the dental treatment tray having at least two walls and a floor, the walls having inner surfaces that, together with the floor, define a well configured to accommodate the at least one of the upper or lower dental arcades and an active agent with suitable electric conductivity;
   at least one electrode located on the inner surface of each of the walls and configured to apply electric current in course of treatment to the active agent in the well of the dental treatment tray;
   at least one light source located on the inner surface of each of the walls and configured to emit light into the well;
   each of the walls comprising a plurality of segments, wherein each segment on one of the walls is aligned with one of the segments on the other one of the walls, and wherein each segment includes at least one of the electrodes and an optical sensor, the optical sensor in each segment configured to monitor a color of one or more teeth within that same segment; and
   a processor operably coupled to the electrodes and the optical sensors, the processor configured to independently control and adjust operation of the electrodes in each segment based on a signal received from the optical sensor in that segment.

2. The apparatus according to claim 1, further comprising a portable unit including:
   at least one of an alternating current (AC) or direct current (DC) power source configured to power the at least one electrode; and
   a DC-current generator.

3. The apparatus according to claim 2, wherein the DC-current generator applies electric current to the at least one electrode immersed into an active agent and wherein the electric current accelerates at least an oxidation reaction.

4. The apparatus according to claim 3, wherein the at least one electrode is embedded inside the walls of the dental treatment tray so as to have an exposed surface to create an electric current in the active agent.

5. The apparatus according to claim 2, wherein the dental treatment tray is connected to the portable unit via a harness.

6. The apparatus according to claim 1, further comprising a portable unit operably coupled to the dental treatment tray, the portable unit comprising at least one of a liquid reservoir for storing a liquid and a gel reservoir for storing a gel, the portable unit being configured to supply the liquid or the gel into the well of the dental treatment tray.

7. The apparatus according to claim 6, further comprising one or more apertures in the walls of the dental treatment tray, the one or more apertures communicating with at least one of the liquid reservoir and the gel reservoir via one or more conduits, and further comprising a processor configured to control: (1) activation of the electrodes and the light sources; and (2) location and rate of introduction of the liquid and the gel into the well.

8. The apparatus according to claim 1 further comprising at least one sensor selected from a group of sensors consisting of a temperature sensor, a liquid level gauge, an oxygen sensor, an optic sensor, and a pH meter, and wherein at least one of the sensors is configured to provide a processor with feedback including real-time treatment parameters regarding ongoing dental treatment, wherein the processor is configured to adjust treatment processes based on the feedback received from the at least one of the sensors.

9. The apparatus according to claim 1, wherein the dental treatment tray comprises piezoelectric elements distributed along the inner surfaces of the walls at a location adjacent distal ends of the walls, the piezoelectric elements protruding from the walls so that when one of the upper and lower dental arcades is positioned in the well and the piezoelectric elements are activated, the piezoelectric elements contact a user's gums and apply a non-abrasive massage to the gums.

10. The apparatus according to claim 1, further comprising a plurality of the electrodes and a plurality of the light sources located on each of the walls, and wherein the electrodes and the light sources are positioned in an alternating fashion along each of the walls.

11. The apparatus according to claim 1, wherein the dental treatment tray comprises permanent magnets adhered to the inner surface of the walls and operative to create a magnetic field inside the well and thus improve the teeth whitening carried out by the electrodes.

12. The apparatus according to claim 1, wherein a first and a second of the dental treatment trays are paired and configured to accommodate both the upper dental arcade and the lower dental arcade concurrently, the first dental treatment tray comprising a first data communication connector and the second dental treatment tray comprising a second data communication connector, the first and second data communication connectors being coupled together to facilitate electrical and data communication between the first and second dental treatment trays.

13. The apparatus according to claim 1 wherein each of the walls extends from the floor to a distal end, and wherein the at least one electrode and the at least one light source on each of the walls is located entirely between the floor of the dental treatment tray and the distal end of the wall on which it is located, and wherein the at least one electrode on the inner surface of a first one of the walls is an anode and the at least one electrode on the inner surface of a second one of the walls is a cathode.

14. The apparatus according to claim 1 further comprising a plurality of partitions extending from the inner surfaces of each of the walls into the well and apportioning each of the walls into the plurality of segments.

15. The apparatus according to claim 1 wherein each of the segments includes at least one aperture, and wherein the processor is configured to introduce an active agent from a reservoir into the well or remove a liquid from the well via one or more of the apertures.

16. An apparatus for electro-chemical dental whitening, said apparatus comprising:
a dental treatment tray configured to be applied to at least one of upper or lower dental arcades, the dental treatment tray having a floor, a front curved wall, and a rear curved wall that collectively define a well, each of the front and rear curved walls having an inner surface that faces the well;
a plurality of partitions extending from the inner surfaces of each of the front and rear curved walls into the well and apportioning each of the front and rear curved walls into a plurality of segments, and wherein each segment on the front curved wall is aligned with one of the segments on the rear curved wall;
at least one electrode and a sensor located with each of the segments of the front and rear curved walls;
a power source operably coupled to and powering each of the electrodes; and
a processor operably coupled to the electrodes and the sensors, the processor configured to independently control and adjust operation of the electrodes in each segment based on a signal received from the sensor in that segment.

17. The apparatus according to claim 16 wherein the sensor located within each of the segments is a color verification sensor, the color verification sensor monitoring changes in a color of one or more teeth.

18. The apparatus according to claim 17 wherein the processor is configured to monitor the color of a plurality of the teeth and analyze color differences between the plurality of teeth based on signals received from the sensors.

* * * * *